:::

(12) United States Patent
Huang et al.

(10) Patent No.: US 12,313,610 B2
(45) Date of Patent: *May 27, 2025

(54) METHOD AND SYSTEM FOR CALIBRATING A GAS DETECTOR

(71) Applicant: Honeywell International Inc., Charlotte, NC (US)

(72) Inventors: Chuang Huang, Shanghai (CN); Jianli Liu, Shanghai (CN); Li Liu, Shanghai (CN)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,583

(22) Filed: Apr. 5, 2024

(65) Prior Publication Data

US 2024/0248070 A1 Jul. 25, 2024

Related U.S. Application Data

(63) Continuation of application No. 17/285,335, filed as application No. PCT/CN2019/114971 on Nov. 1, 2019, now Pat. No. 11,977,061.

(51) Int. Cl.
G01N 33/00 (2006.01)

(52) U.S. Cl.
CPC ..... G01N 33/0006 (2013.01); G01N 33/0016 (2013.01)

(58) Field of Classification Search
CPC .................................................. G01N 33/0006
See application file for complete search history.

(56) References Cited

U.S. PATENT DOCUMENTS

| | | | |
|---|---|---|---|
| 7,141,090 B2 | 11/2006 | Marek et al. |
| 2007/0144250 A1 | 6/2007 | Ramsesh |
| 2010/0300180 A1 | 12/2010 | Bosi et al. |
| 2015/0177205 A1 | 6/2015 | Arias et al. |
| 2021/0131903 A1 | 5/2021 | Ghasemvand et al. |

FOREIGN PATENT DOCUMENTS

| | | |
|---|---|---|
| CN | 204556597 U | 8/2015 |
| CN | 106645587 A | 5/2017 |
| CN | 106770738 A | 5/2017 |
| CN | 207263711 U | 4/2018 |
| CN | 108680711 A | 10/2018 |

(Continued)

OTHER PUBLICATIONS

U.S. Appl. No. 17/285,335, filed Apr. 14, 2021, 20220003729, Allowed.

(Continued)

*Primary Examiner* — Alexander A Mercado
(74) *Attorney, Agent, or Firm* — Alston & Bird LLP

(57) ABSTRACT

A calibration system for calibrating a gas detector includes a control unit and a temperature regulation assembly electrically connected with the control, a temperature sensor electrically connected with the control unit, a set of valves comprising a first valve, a second valve, and a third valve, and a feedback conduit. The control unit is configured to determine whether a temperature of the gas detector is within a predefined temperature range and calibrate the gas detector in an instance in which the temperature is within the predefined temperature range.

20 Claims, 6 Drawing Sheets

(56) References Cited

FOREIGN PATENT DOCUMENTS

CN    110220574 A    9/2019
WO    2004/097399 A2    11/2004

OTHER PUBLICATIONS

Communication about intention to grant a European patent Mailed on Jul. 19, 2024 for EP Application No. 19944649, 6 page(s).
CA Office Action Mailed on Dec. 8, 2022 for CA Application No. 3113159.
CA Office Action Mailed on Sep. 21, 2023 for CA Application No. 3113159, 3 page(s).
European Search Report Mailed on Mar. 14, 2022 for EP Application No. 19944649.3, 8 page(s).
Intention to grant Mailed on Mar. 5, 2024 for EP Application No. 19944649, 9 page(s).
International Search Report and Written Opinion mailed on Aug. 11, 2020 for WO Application No. PCT/CN19/114971.
Non-Final Rejection Mailed on Sep. 7, 2023 for U.S. Appl. No. 17/285,335, 12 page(s).
Notice of Allowance and Fees Due (PTOL-85) Mailed on Jan. 10, 2024 for U.S. Appl. No. 17/285,335, 8 page(s).
Notice of Allowance and Fees Due (PTOL-85) Mailed on Mar. 27, 2024 for U.S. Appl. No. 17/285,335, 2 page(s).
Supplementary European search report Mailed on Mar. 14, 2022 for EP Application No. 19944649, 8 page(s).
Decision to grant a European patent Mailed on Dec. 5, 2024 for EP Application No. 19944649, 2 page(s).
Extended European Search Report Mailed on Mar. 21, 2025 for EP Application No. 24222849, 9 page(s).

METHOD AND SYSTEM FOR CALIBRATING A GAS DETECTOR

This application is a continuation application of and claims priority to U.S. application Ser. No. 17/285,335, filed Apr. 14, 2021, which is a national stage application of PCT/CN2019/114971, filed Nov. 1, 2019, each of which are hereby incorporated by reference in their entirety.

TECHNOLOGICAL FIELD

Exemplary embodiments of the present disclosure relate generally to a gas detector and, more particularly, to methods and systems for calibrating a gas detector.

BACKGROUND

Typically, gas detectors may be deployed in different work environments and industries for detecting presence of unwanted and harmful gases in the ambient air. Such gases may be present in the ambient air due to, amongst other reasons, a leakage in a gas container or a pipe line that stores or supplies the gases. The gas detectors may monitor the concentration of such gases in the ambient air and issue an alert when the concentration of the gases exceed acceptable levels.

There may be different types of gas detectors used for detecting the gases. Some examples of the gas detectors may include, but are not limited to, electrochemical cell-based gas detectors, acoustic gas detectors, solid state gas detector, and/or the like. Usually, the gas detectors detect gases based on at least a chemical reaction between the gas and one or more electrodes in a gas detector. Typically, the rate of chemical reaction in such a gas detector may vary based on one or more parameters such as temperature, pressure, and/or the like. For seamless operation of the gas detectors in the work environment, it may be required to calibrate such gas detectors, prior to deployment, such that the calibrated gas detectors are able to operate in varying work environments.

Applicant has identified a number of deficiencies and problems associated with methods and systems of calibrating a gas detector. Through applied effort, ingenuity, and innovation, many of these identified problems have been solved by developing solutions that are included in embodiments of the present disclosure, many examples of which are described in detail herein.

BRIEF SUMMARY

According to the embodiments disclosed herein, a gas detector calibration system is disclosed. The gas detector calibration system comprises a control unit and a temperature regulation assembly. The temperature regulation assembly is electrically connected with the control unit and has an inlet and an outlet. The temperature regulation assembly is configured to receive ambient air through the inlet of the temperature regulation assembly and modify a temperature of the ambient air. After regulating the temperature of the ambient air, the ambient air is supplied to a gas detector through the outlet of the temperature regulation assembly. The gas detector calibration system comprises a temperature sensor that is electrically connected with the control unit and is placed in proximity to the gas detector to measure a temperature of the gas detector. The temperature sensor sends a signal indicative of the temperature of the gas detector to the control unit. The control unit determines whether the temperature of the gas detector is within a predefined temperature range. When the temperature of the gas detector is within the predefined temperature range, the gas detector is calibrated using a calibration gas.

According to the embodiments disclosed herein, a method for calibrating the gas detector is disclosed. The method comprises causing, by the control unit, the temperature regulation assembly to modify the temperature of the ambient air supplied to the gas detector. The method comprises receiving, by the control unit, a signal indicative of the temperature of the gas detector from the temperature sensor and determining, by the control unit, whether the temperature of the gas detector is within the predefined temperature range. After determining that the temperature is within the predefined temperature range, the method comprises calibrating the gas detector by using the calibration gas.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
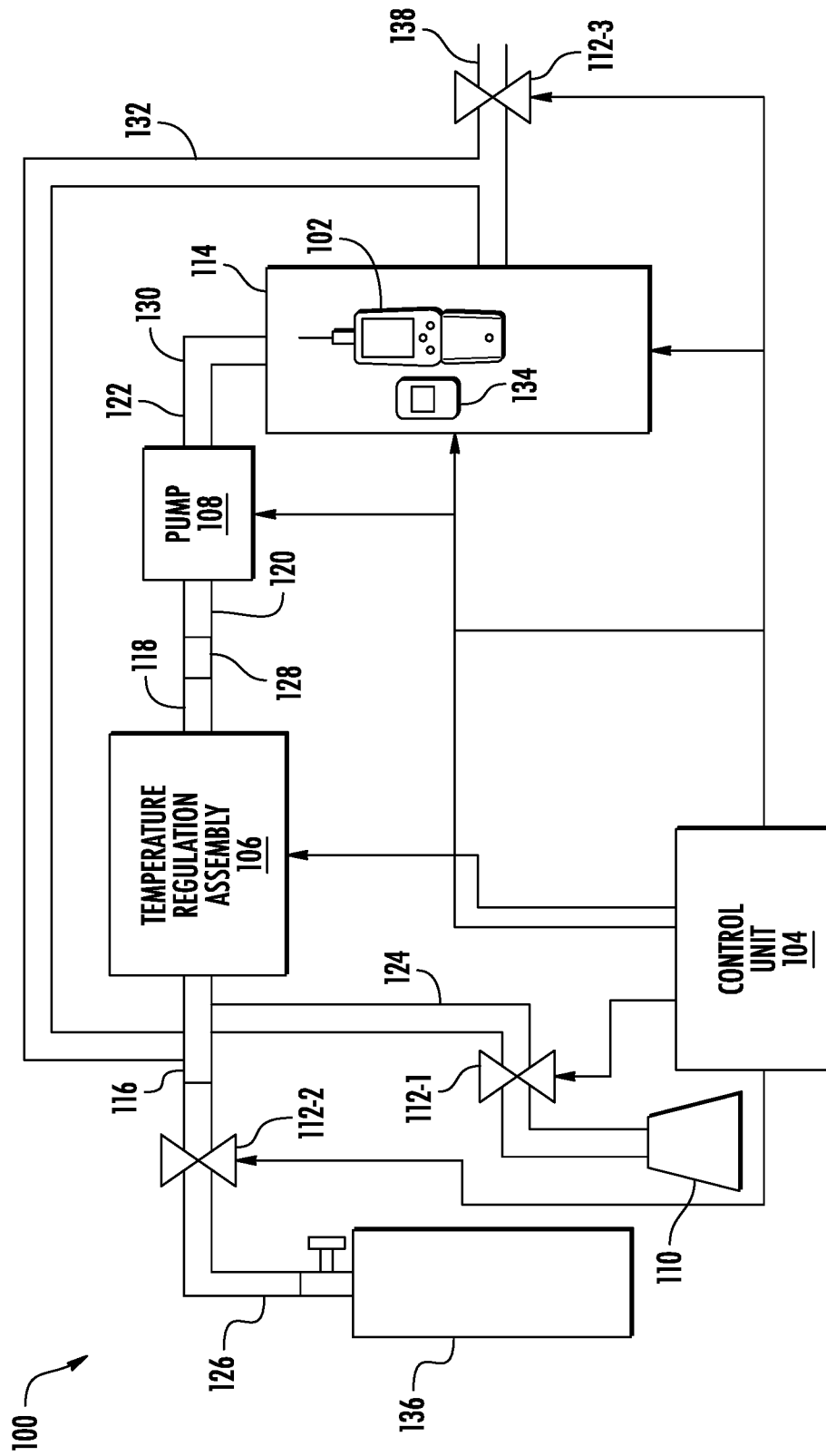
FIG. 1 illustrates a gas detector calibration system, according to one or more embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The term "comprising" means including but not limited to and should be interpreted in the manner it is typically used in the patent context. Use of broader terms such as "comprises," "includes," and "having" should be understood to provide support for narrower terms such as "consisting of," "consisting essentially of," and "comprised substantially of."

The phrases "in one embodiment," "according to one embodiment," and the like generally mean that the particular feature, structure, or characteristic following the phrase may be included in at least one embodiment of the present disclosure, or may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may" "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The "gas detector" as described in the embodiments herein refers to a device for measuring and indicating concentration of a gas. The gas detector has a sensor that aids in measuring the concentration of the gas in the ambient air. The gas detector is generally a stationary or a portable unit that may be battery operated. The gas detector has one or more audible or visible indicators, such as alarms, lights or a combination of signals to indicate a level of the gas. The gas detector can detect one type of gas or more than one type of gases at once. There are different types of gas detectors based on type of sensors used. Some examples of the gas detector may include, but are not limited to, Electrochemical (EC) sensors, Lower Explosive Limit (LEL) sensors, Non-dispersive Infrared (NDIR) sensors, and Photoionization Detector (PID).

The "temperature sensor" is used for detecting a temperature of a device or an ambient. The temperature sensor may generate an electrical signal corresponding to the detected temperature. Some examples of the temperature sensor may include, but are not limited to, a thermocouple, a resistive temperature measuring device, a bimetallic device, a digital thermometer, and a change of state sensor.

The "gas" may either be toxic, flammable or asphyxiant in nature that may be harmful for users working at a workplace. Presence of the gas above an acceptable level may be undesirable and may lead to a hazardous event. Most common toxic gases include, but are not limited to, carbon monoxide, chlorine, nitrogen oxide and hydrogen sulfide.

The "calibration gas" corresponds to a gas in a pure form that is used for calibrating the gas detector. The calibration gas may also have a mixture of gases that is generally compressed and supplied to the gas detector for calibration. An example of the calibration gas may include a pure nitrogen gas used for calibrating a carbon dioxide gas detector.

Gas detectors are installed at different work environments and industries to detect unwanted gases and prevent a gas hazard. The gases may be present in the ambient air due to, amongst other reasons, a leakage in a gas container or a pipe line that stores or supplies the gases. The gas detectors constantly monitor the concentration of such gases and alert users when the concentration of the gases is above the acceptable level.

Usually, the gas detectors may be calibrated prior to deployment, such that the calibrated gas detector is able to operate in varying work environments. For example, the gas detector may be calibrated to operate in different temperature conditions. The gas detectors, upon deployment in a work environment, constantly detect gases and over a period, develop issues such as material consumption and faulty or erroneous operation. Other factors, such as exposure to toxic gases and temperature variations may also affect the operation of the gas detectors. For instance, the Electrochemical (EC) sensors may have material consumption issues and the PID and the NDIR sensors may have component degradation issues. Generally, the gas detectors are calibrated onsite at regular time intervals to prevent such issues. The calibration is performed at a temperature of the work environment and any variations in the temperature can cause improper calibration and lead to erroneous operation of the gas detectors during deployment.

The apparatuses described herein disclose a gas detector calibration system that may calibrate a gas detector to operate at different temperature conditions of work environments. The gas detector calibration system comprises a control unit, a temperature regulation assembly having an inlet and an outlet, a temperature sensor, a gas detector, a pump having a pump inlet and a pump outlet, an atmospheric filter, and a plurality of valves.

In an example embodiment, the inlet of the temperature regulation assembly is fluidly coupled to the atmospheric filter. The inlet of the temperature regulation assembly is fluidly coupled to a gas container storing calibration gas. In an example, the outlet of the temperature regulation assembly is fluidly coupled to the pump inlet of the pump. The pump outlet of the pump is fluidly coupled to a chamber. The chamber may be a housing or a container within which the gas detector and the temperature sensor may be positioned. In some examples, the gas detector includes the temperature sensor that is configured to measure a temperature of the gas detector. In an alternative embodiment, the temperature sensor is positioned in proximity to the gas detector to detect the temperature of the gas detector.

In an example embodiment, the temperature regulation assembly, the pump, and the temperature sensor are electrically connected to the control unit. In some examples, the control unit is configured to control the operation of the temperature regulation assembly, the pump, and the temperature sensor.

In an example embodiment, prior to calibrating the gas detector, the control unit may activate the pump. Since the pump is fluidly coupled to the temperature regulation assembly and the temperature regulation assembly is fluidly coupled to the ambient through the atmospheric filter, therefore, when the control unit activates the pump, the temperature regulation assembly receives the ambient air from the ambient. In an example embodiment, a first valve controls flow of the ambient air from the atmospheric filter to the temperature regulation assembly, and the control unit may activate the first valve to an open state to allow flow of the ambient air from the atmospheric filter to the temperature regulation assembly.

Concurrently, the control unit may instruct the temperature regulation assembly to modify the temperature of the received ambient air based on a predefined temperature range, such that the temperature of the ambient air is within the predefined temperature range. In an example embodiment, the predefined temperature range may correspond to a temperature range within which the gas detector is to be calibrated. For example, the control unit may instruct the temperature regulation assembly to reduce the temperature of the ambient air. In some examples, the control unit may instruct the temperature regulation assembly to heat the ambient air. Accordingly, in some examples, the temperature regulation assembly generates ambient air having a first temperature. Since the pump is operating in an active state and the inlet of the pump is fluidly coupled to the outlet of the temperature regulation assembly, the pump receives the ambient air at a first temperature from the temperature regulation assembly. In an example embodiment, the first temperature may correspond to a temperature at which the gas detector is to be calibrated. In some examples, the predefined temperature range includes the first temperature. In an alternative embodiment, the control unit may determine the predefined temperature range based on the first temperature at which the temperature regulation assembly is being operated. For example, the control unit may determine the predetermined temperature range as ±10 degrees of the first temperature.

The pump forwards the ambient air at the first temperature to the gas detector through the pump outlet. The ambient air, at the first temperature, passes through the chamber. As the ambient air passes through the chamber, the ambient air modifies an initial temperature of the gas detector. In an example embodiment, the initial temperature may correspond to a temperature of the gas detector prior to calibrating the gas detector.

In an example embodiment, the temperature sensor, adjacent to the gas detector, determines a second temperature of the gas detector at regular intervals. In an example embodiment, the second temperature of the gas detector corresponds to a current temperature of the gas detector while the ambient air at the first temperature passes through the gas detector. Further, the temperature sensor transmits a signal indicative of the second temperature of the gas detector to the control unit.

In an example embodiment, the control unit determines whether the second temperature of the gas detector is equal to the first temperature or within the predefined temperature range. In an instance in which the second temperature of the gas detector is within the predefined temperature range, the control unit deactivates the pump to stop flow of the ambient air through the gas detector. Thereafter, the control unit causes flow of a calibration gas to the gas detector for calibrating the gas detector at the determined temperature. In an example embodiment, a second valve controls flow of the calibration gas to the temperature regulation assembly, and the control unit may activate the second valve to an open state to allow flow of the calibration gas to the temperature regulation assembly.

The aforementioned process can be used to calibrate the gas detector in the predefined temperature range that is optimum for calibrating the gas detector. Calibrating the gas detector at a temperature, such as the second temperature, reduces variations in the temperature during calibration thereby eliminating issues related to erroneous operation of the gas detector during calibration.

The details regarding additional components and functioning of various components of the gas detector calibration system is explained further with respect to description of FIG. 1.

FIG. 1 illustrates a gas detector calibration system 100, according to one or more embodiments described herein. In an example embodiment, the gas detector calibration system 100 may be capable of calibrating gas detectors, such as a gas detector 102.

In an example embodiment, the gas detector calibration system 100 may include the gas detector 102, a control unit 104, a temperature regulation assembly 106, a pump 108, an atmospheric filter 110, a plurality of valves 112-1, 112-2 and 112-3, and a chamber 114.

In an example embodiment, the temperature regulation assembly 106 may include suitable components such as a heating unit and a cooling unit that may be configured to modify a temperature of a gas passing through the temperature regulation assembly 106 based on an instruction received from the control unit 104 about the temperature. For example, the temperature regulation assembly 106 may modify the temperature of ambient air that passes through the temperature regulation assembly 106. The temperature regulation assembly 106 has an inlet 116 and an outlet 118.

In an example embodiment, the inlet 116 of the temperature regulation assembly 106 may be configured to receive ambient air through the atmospheric filter 110. In some examples, the atmospheric filter 110 is fluidly coupled to the temperature regulation assembly 106 through a first conduit 124 and is positioned upstream of the temperature regulation assembly 106. In an example embodiment, the atmospheric filter 110 is to receive the ambient air by removing dust particles from the ambient air and supply the ambient air to the temperature regulation assembly 106. In an example embodiment, the atmospheric filter 110 may be one of an electrostatic filter, an activated carbon filter, and an Ultraviolet (UV) light filter. In an example embodiment, to control the flow of the ambient air to the temperature regulation assembly 106, the first conduit 124 may have a first valve 112-1 that is positioned downstream of the atmospheric filter 110, (along the flow of the ambient air and upstream of the temperature regulation assembly 106). In an example embodiment, the first valve 112-1 may have an open state and a closed state. In the open state, the valve 112-1 allows flow of the ambient air through the first conduit 124, and in the closed state, the valve 112-1 stops the flow of the ambient air through the first conduit 124. The first valve 112-1 may be a gate valve, a globe valve, a plug valve, a ball valve, a butterfly valve, a swing check valve, a diaphragm valve, a pinch valve, a safety valve, and a relief valve.

In some examples, the inlet 116 of the temperature regulation assembly 106 is further coupled to a gas container 136 through a second conduit 126. In some examples, the gas container 136 may be a storage container to store a calibration gas in a compressed form. The gas container 136 may have a valve opening (not shown) through which the gas container 136 may supply the calibration gas. In some examples, the second conduit 126 may be coupled to the valve opening of the gas container 136. Similar to the first conduit 124, the second conduit 126 includes a second valve 112-2 that may be configured to control the flow of the calibration gas through the second conduit 126 to the temperature regulation assembly 106. In an example embodiment, the second valve 112-2 is similar to the first valve 112-1 in structure and function.

In an example embodiment, the outlet 118 of the temperature regulation assembly 106 may be fluidly coupled to a pump inlet 120 through a third conduit 128. Further, a pump outlet 122 may be coupled to the chamber 114 through a fourth conduit 130. In an example embodiment, the pump 108 may cause the ambient air and the calibration gas to flow through the temperature regulation assembly 106. Further, the pump 108 may cause the ambient air or the calibration gas to flow through the other components of the system 100 connected downstream of the pump 108. For example, the pump 108 may cause the ambient air or the calibration gas to flow through the chamber 114. Examples of the pump 108 may include, but are not limited to, a centrifugal pump, a vertical centrifugal pump, a horizontal centrifugal pump, a diaphragm pump, a gear pump, a peristaltic pump, a Lobe pump, and a piston pump.

In an example embodiment, the chamber 114 may be a housing or an encasing to receive the gas detector 102 and a temperature sensor 134. The chamber 114 provides a closed environment to the gas detector 102 for calibration and insulates the gas detector 102 from outside temperature during calibration. The chamber 114 has a first opening to receive an end of the fourth conduit 130 and a second opening to receive an end of a feedback conduit 132. In an example embodiment, the gas detector 102 is positioned in proximity to the first opening of the chamber 114 and the temperature sensor 134 is positioned adjacent to the gas detector 102 for determining temperature of the gas detector 102.

In an example embodiment, the chamber 114 is coupled to the inlet 116 of the temperature regulation assembly 106 through the feedback conduit 132. Further, the feedback conduit 132 has an exhaust conduit 138 and a third valve 112-3 is connected to the exhaust conduit 138. In an example embodiment, the third valve 112-3 is similar to the other two valves 112-1 and 112-2 in structure and function.

In an example embodiment, the temperature regulation assembly 106, the pump 108, the temperature sensor 134, the valves 112-1, 112-2, and 112-3 are electrically connected to the control unit 104. In some examples, the control unit 104 is configured to control the operation of the temperature regulation assembly 106 by sending a signal regarding the first temperature at which the temperature regulation assembly 106 is to be operated for modifying temperature of the ambient air, as is further described in FIG. 3. In an example embodiment, the control unit 104 is configured to activate the pump 108. The control unit 104 is configured to operate the valves 112-1, 112-2 and 112-3 to switch states between an open state and a closed state to control the flow of the ambient air or the calibration gas through the system 100, as described in FIG. 3. The control unit 104 is configured to receive signals from the temperature sensor 134 regarding the second temperature and any other temperature between the first temperature and the second temperature of the gas detector 102 during modification of the temperature of the gas detector 102. In an example embodiment, the first temperature corresponds to a temperature at which the gas detector 102 is to be calibrated, and the second temperature corresponds to a current temperature of the gas detector 102 while the ambient air at the first temperature passes through the gas detector 102.

The details of the components of the control unit 104 and the working of the components is described with reference to FIG. 2, FIG. 3 and FIG. 4.

Figure 2:
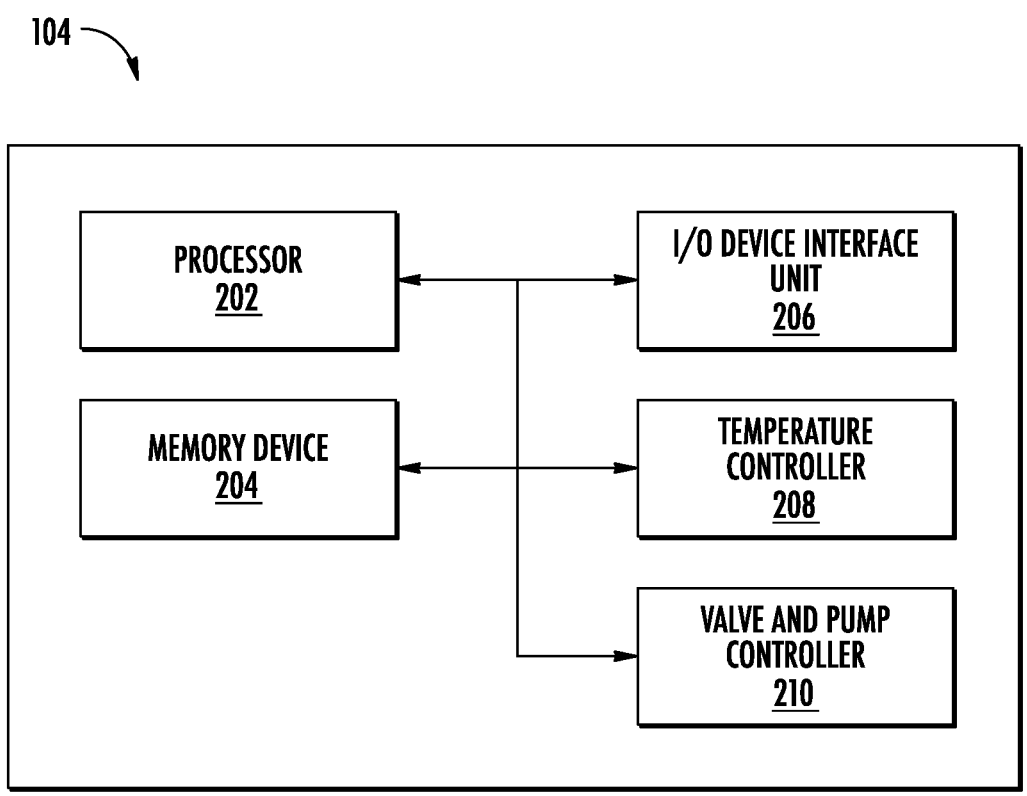
FIG. 2 illustrates a block diagram of components of a control unit, according to one or more embodiments described herein.

FIG. 2 illustrates a block diagram of the control unit 104, according to one or more embodiments described herein. The control unit 104 includes a processor 202, a memory device 204, a first input/output (I/O) device interface unit 206, a temperature controller 208, and a valve and pump controller 210.

The processor 202 may be embodied as means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC) or field programmable gate array (FPGA), or some combination thereof. Accordingly, although illustrated in FIG. 2 as a single processor, in an embodiment, the processor 202 may include a plurality of processors and signal processing modules. The plurality of processors may be embodied on a single electronic device or may be distributed across a plurality of electronic devices collectively configured to function as the circuitry of the control unit 104. The plurality of processors may be in operative communication with each other and may be collectively configured to perform one or more functionalities of the circuitry of the control unit 104, as described herein. In an example embodiment, the processor 202 may be configured to execute instructions stored in the memory device 204 or otherwise accessible to the processor 202. These instructions, when executed by the processor 202, may cause the circuitry of the control unit 104 to perform one or more of the functionalities as described herein.

Whether configured by hardware, firmware/software methods, or by a combination thereof, the processor 202 may include an entity capable of performing operations according to embodiments of the present disclosure while configured accordingly. Thus, for example, when the processor 202 is embodied as an ASIC, FPGA or the like, the processor 202 may include specifically configured hardware for conducting one or more operations described herein. Alternatively, as another example, when the processor 202 is embodied as an executor of instructions, such as may be stored in the memory device 204, the instructions may specifically configure the processor 202 to perform one or more algorithms and operations described herein.

Thus, the processor 202 used herein may refer to a programmable microprocessor, microcomputer or multiple processor chip or chips that can be configured by software instructions (applications) to perform a variety of functions, including the functions of the various embodiments described above. In some devices, multiple processors may be provided which are dedicated to wireless communication functions, and one processor may be provided which is dedicated to running other applications. Software applications may be stored in the internal memory before they are accessed and loaded into the processors. The processors may include internal memory sufficient to store the application software instructions. In many devices, the internal memory may be a volatile or nonvolatile memory, such as flash memory, or a mixture of both. The memory can also be located internal to another computing resource (e.g., enabling computer readable instructions to be downloaded over the Internet or another wired or wireless connection).

The memory device 204 may include suitable logic, circuitry, and/or interfaces that are adapted to store a set of instructions that is executable by the processor 202 to perform predetermined operations. Some of the commonly known memory implementations include, but are not limited to, a hard disk, random access memory, cache memory, read only memory (ROM), erasable programmable read-only memory (EPROM), electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an example embodiment, the memory device 204 may be integrated with the processor 202 on a single chip, without departing from the scope of the disclosure.

The I/O device interface unit 206 may include suitable logic and/or circuitry that may be configured to communicate with the one or more components of the gas detector calibration system 100, in accordance with one or more device communication protocols such as, but not limited to, I2C communication protocol, Serial Peripheral Interface (SPI) communication protocol, Serial communication protocol, Control Area Network (CAN) communication protocol, and 1-Wire® communication protocol. In an example embodiment, the I/O device interface unit 206 may communicate with the temperature sensor 134 and the valves 112-1, 112-2 and 112-3 for facilitating the transmission and reception of the data and signal to and from the temperature sensor 134 and the valves 112-1, 112-2 and 112-3, as is further described in conjunction with FIG. 3. Some examples of the I/O device interface unit 206 may include, but are not limited to, a Data Acquisition (DAQ) card, an electrical drives driver circuit, and/or the like.

Figure 3:
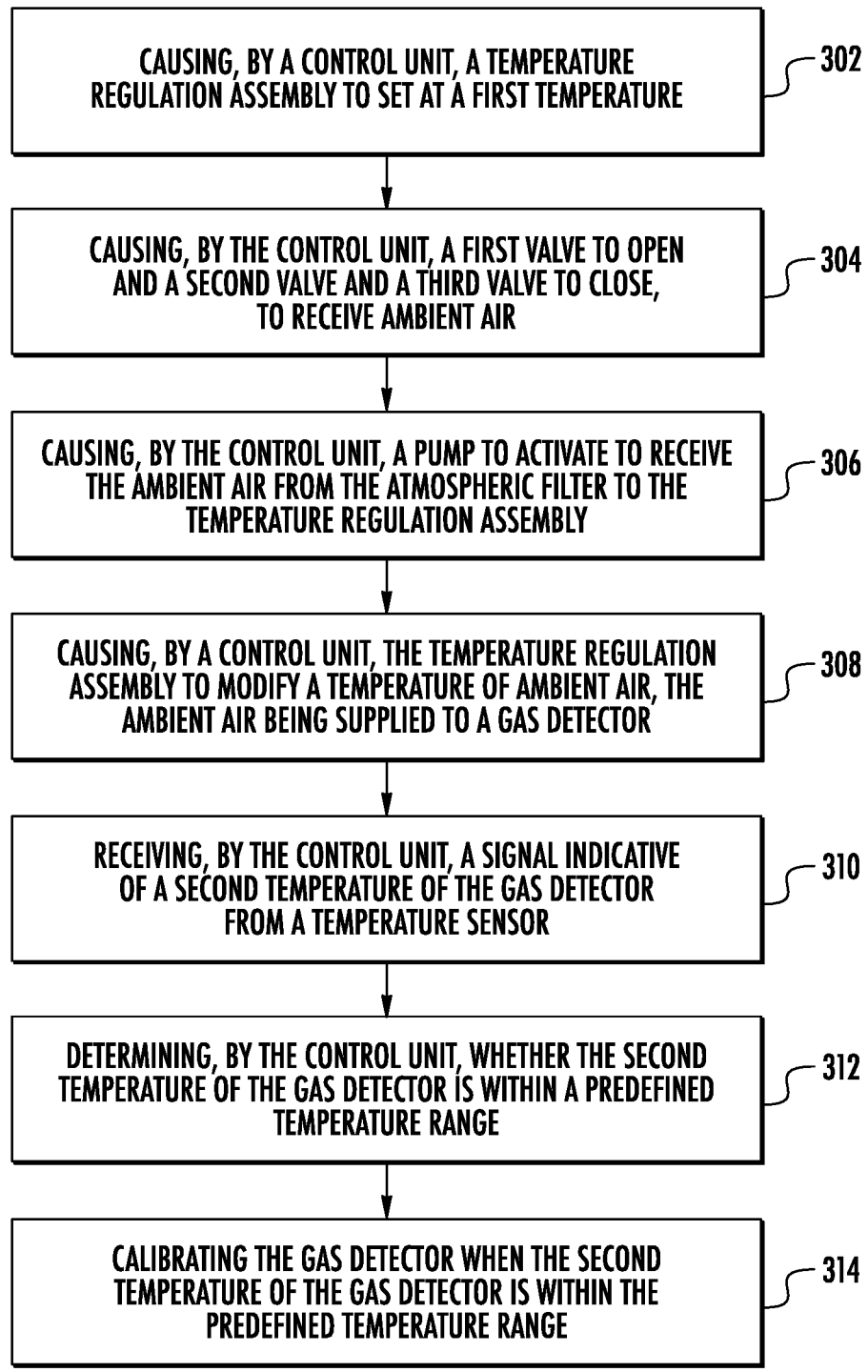
FIG. 3 illustrates a flow chart of a method for calibrating the gas detector, according to one or more embodiments described herein.

The temperature controller 208 may include suitable logic and/or circuitry that may instruct the temperature regulation assembly 106 to operate at a particular temperature (e.g., first temperature), as is further described in FIG. 3. The temperature controller 208 may be configured to receive a signal from the temperature sensor indicative of the temperature, as is further described in FIG. 3. Further the temperature controller may be configured to compare the temperature with the predefined temperature, as is further described in FIG. 3. The temperature controller 208 may be implemented using one or more hardware components, such as, but not limited to, FPGA, ASIC, and the like.

The valve and pump controller 210 may include suitable logic and/or circuitry that may operate the pump 108 to operate and control flow of the ambient air and the calibration gas to the gas detector 102, as is further described in conjunction with FIG. 3. The valve and pump controller 210 may be further configured to switch states of the valves 112-1, 112-2 and 112-3 between an open state and a closed state to control flow of the ambient air and the calibration gas in the gas detector calibration system 100. The valve and pump controller 210 may be implemented using one or more hardware components, such as, but not limited to, FPGA, ASIC, and the like.

The operation of the control unit 104 is described later in conjunction with FIG. 3.

Referring to FIG. 3, in conjunction with FIG. 1 and FIG. 2, a flowchart illustrating operations for calibrating a gas detector, such as the gas detector 102, is described. FIG. 3 shows the flowchart illustrating operation of the control unit, in accordance with the example embodiments described herein.

Turning first to step 302, the gas detector calibration system 100 includes means, such as, the control unit 104, the processor 202, the temperature controller 208, and/or the like, causing the temperature regulation assembly 106 to operate at a first temperature. For this, the temperature controller 208 is configured to send a signal to the temperature regulation assembly 106 regarding the first temperature at which the temperature regulation assembly 106 is to be operated. In an example embodiment, the temperature controller 208 may receive an input regarding the first temperature from a user. In an alternative embodiment, the temperature controller 208 may receive the first temperature from another temperature sensor (not shown) installed in a work environment.

At step 304, the gas detector calibration system 100 includes means, such as, the control unit 104, the processor 202, the valve and pump controller 210, and/or the like, to cause opening of the first valve 112-1 by activating an open state of the valve 112-1 and closing of the second valve 112-2 and the third valve 112-3 by activating closed states of the second valve 112-2 and the third valve 112-3. In an example embodiment, each of the valves 112-1, 112-2 and 112-3 may have an open state and a closed state. In the open state, the valves 112-1, 112-2 and 112-3 allow flow of the ambient air or calibration gas. In the closed state, the valves 112-1, 112-2 and 112-3 stop the flow of the ambient air or the calibration gas.

At step 306, the gas detector calibration system 100 includes means, such as, the control unit 104, the processor 202, the valve and pump controller 210, and/or the like, to activate the pump 108 to cause the ambient air to flow to the temperature regulation assembly 106 from the atmospheric filter 110.

Thereafter, at step 308, the temperature controller 208 is configured to cause the temperature regulation assembly 106 to modify a temperature of ambient air based on the predefined temperature range to bring the temperature of the ambient air to the first temperature. The predefined temperature range, as explained earlier, may be an optimum range for the calibration of the gas detector 102 and may be stored in the temperature controller 208. The temperature of the ambient air may be modified, for instance, by passing the ambient air through either the heating unit or the cooling unit of the temperature regulation assembly 106. In an example, the predefined temperature range is from about 30° C. to about 60° C. For instance, if the room temperature is around 20° C., then the ambient air is passed through the heating unit to heat the ambient air to reach a temperature within the predefined temperature range.

After regulating the temperature, the pump 108 receives the ambient air from the temperature regulation assembly 106 through the outlet 118, the third conduit 128 and the pump inlet 120 and supplies the ambient air to the gas detector 102 through the pump outlet 122 and the fourth conduit 130. In an alternative embodiment, the pump 108 supplies the ambient air to the chamber 114 having the gas detector 102 and the temperature sensor 134. The gas detector 102 is positioned in proximity to the first opening of the chamber 114 and the temperature sensor 134 is positioned adjacent to the gas detector 102.

After supplying the ambient air to the gas detector 102, the temperature sensor 134 determines the temperature of the gas detector 102. As the ambient air with the modified temperature passes through the gas detector 102, the temperature of the gas detector 102 is modified from the initial temperature to the second temperature. The temperature sensor 134 determines the second temperature of the gas detector 102.

At step 310, the temperature controller 208 receives a signal indicative of the temperature, for instance the second temperature, of the gas detector 102 from the temperature sensor 134. In an example embodiment, the temperature controller 208 causes the temperature sensor 134 to determine the temperature of the gas detector 102 and send the signal after every preset period. For example, the temperature sensor 134 may determine the temperature after every 20 seconds and send a corresponding signal to the temperature controller 208.

At step 312, the processor 202 may determine if the second temperature of the gas detector 102 is within the predefined temperature range. In an embodiment, the processor 202 may determine if the second temperature is equal to the first temperature. If the processor 202 determines the second temperature is not within the predefined temperature range, then the valve and pump controller 210 is configured to allow flow of the ambient air back to the inlet 116 of the temperature regulation assembly 106 through the feedback conduit 132, by keeping the third valve 112-3 closed. The ambient air is again heated or cooled to bring the temperature of the ambient air within the predefined temperature.

The pump 108 receives the ambient air and supplies the ambient air to the gas detector 102. The temperature sensor 134 then determines a third temperature of the gas detector 102 and sends a signal to the temperature controller 208. Thereafter, valve and pump controller 210 is configured to operate the third valve 112-3 to open and release the ambient air outside the gas detector calibration system 100 through the exhaust conduit 138 of the feedback conduit 132, when the third temperature of the gas detector 102 is within the predefined temperature range or equal to the first temperature. Further, the valve and pump controller 210 is configured to close the first valve 112-1 by activating the first valve 112-1 to a closed state to stop the flow of the ambient air, and activating the third valve 112-3 to a closed state?, and opening the second valve 112-2 by activating the second valve 112-2 to an open state to allow the calibration gas to flow through the second conduit 126 for calibration of the gas detector 102.

Thereafter, at step 314, the gas detector calibration system 100 includes means, such as the control unit 104, the processor 202, the valve and pump controller 210, and/or the like, to supply the calibration gas to the gas detector 102 for calibration by activating an open state of the second valve 112-2 for flow of the calibration gas from the gas container 136 to the temperature regulation assembly 106 and then supplying the calibration gas from the temperature regulation assembly 106 to the gas detector 102.

In an example embodiment, the valve and pump controller 210 is configured to supply the calibration gas to the temperature regulation assembly 106 prior to supplying the calibration gas to the gas detector 102, by activating the second valve 112-2 in an open state. The calibration gas is supplied to the temperature regulation assembly 106 to modify the temperature of the calibration gas to the first temperature.

The temperature of the calibration gas is modified to bring the temperature of the calibration gas within the predefined temperature range. The regulation of the temperature of the calibration gas may be performed such that the calibration gas has the same temperature as the gas detector 102, as the temperature difference between the gas detector 102 and the calibration gas may cause error during calibration. After modifying the temperature of the calibration gas, the valve and pump controller 210 is configured to cause the pump 108 to receive the calibration gas from the temperature regulation assembly 106 and supply the calibration gas to the gas detector 102 for calibration. During the calibration, the calibration gas having a predetermined concentration is supplied to the gas detector 102. The processor 202 may receive a calibration result from the gas detector 102 in response to the calibration gas being supplied to the gas detector 102. The calibration result is indicative of actual calibration of the gas detector 202 achieved after the calibration gas, having the predetermined concentration, is supplied to the gas detector 102. The processor 202 may then compare the calibration result with the predetermined concentration of the calibration gas to determine if there is an error in the calibration. In an example embodiment, the error is indicative of a difference between the actual calibration of the gas detector 102 and a calibration to be achieved in response to the predetermined concentration of the calibration gas. Thereafter, the processor 202 may cause the gas detector 102 to correct based on the error in the calibration.

Figure 4:
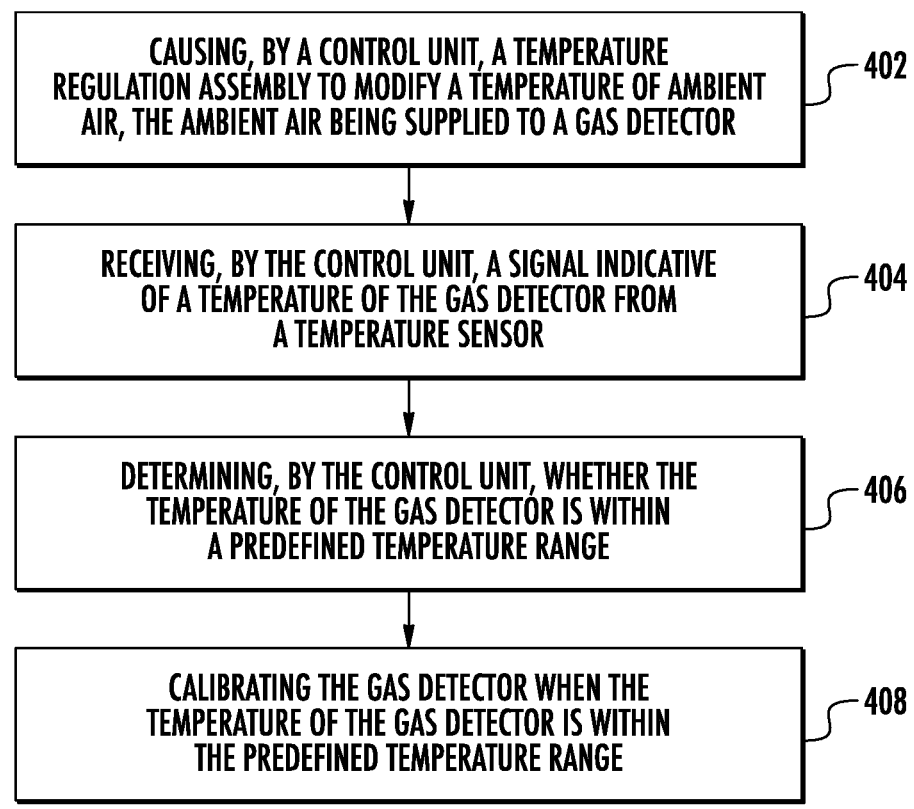
FIG. 4 illustrates a flow chart of another method for calibrating the gas detector, according to one or more embodiments described herein.

FIG. 4 illustrates a flowchart for calibrating a gas detector, such as the gas detector 102, in accordance with the example embodiments described herein. At step 402, the gas detector calibration system 100 includes means, such as the control unit 104, the processor 202, the temperature controller 208, and/or the like, to cause the temperature regulation assembly 106 to modify a temperature of the ambient air. The ambient air is being supplied to the gas detector 102. At step 404, the temperature controller 208 is configured to receive a signal from the temperature sensor 134. The signal is indicative of the temperature of the gas detector 102 after supplying the ambient air to the gas detector 102.

At step 406, the processor 202 determines if the temperature of the gas detector 102 is within the predefined temperature range. If the temperature is within the predefined temperature range, the valve and pump controller 210 is configured to open the second valve 112-2 to receive the calibration gas for calibration of the gas detector 102, at step 408.

FIG. 3 and FIG. 4 illustrate example flowcharts describing operations performed in accordance with example embodiments of the present disclosure. It will be understood that each block of the flowcharts, and combinations of blocks in the flowcharts, may be implemented by various means, such as devices comprising hardware, firmware, one or more processors, and/or circuitry associated with execution of software comprising one or more computer program instructions. For example, one or more of the procedures described above may be embodied by computer program instructions residing on a non-transitory computer-readable storage memory. In this regard, the computer program instructions which embody the procedures described above may be stored by a memory of an apparatus employing an embodiment of the present disclosure and executed by a processor of the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. When executed, the instructions stored in the computer-readable storage memory produce an article of manufacture configured to implement the various functions specified in the flowchart blocks. Moreover, execution of a computer or other processing circuitry to perform various functions converts the computer or other processing circuitry into a machine configured to perform an example embodiment of the present disclosure. Accordingly, the operations set forth in the flowcharts define one or more algorithms for configuring a computer or processor, to perform an example embodiment. In some cases, a general-purpose computer may be provided with an instance of the processor which performs algorithms described in one or more flowcharts to transform the general-purpose computer into a machine configured to perform an example embodiment.

Accordingly, the described flowchart blocks support combinations of means for performing the specified functions and combinations of operations for performing the specified functions. It will also be understood that one or more flowchart blocks, and combinations of flowchart blocks, can be implemented by special purpose hardware-based computer systems which perform the specified functions, or combinations of special purpose hardware that execute computer instructions.

In some example embodiments, certain operations described herein may be modified or further amplified as described below. Moreover, in some embodiments, additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art, the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may in some instances, be construed in the plural.

In one or more example embodiments, the functions described herein may be implemented by special-purpose hardware or a combination of hardware programmed by firmware or other software. In implementations relying on firmware or other software, the functions may be performed as a result of execution of one or more instructions stored on one or more non-transitory computer-readable media and/or one or more non-transitory processor readable media. These instructions may be embodied by one or more processor-executable software modules that reside on the one or more non-transitory computer-readable or processor-readable storage media. Non-transitory computer-readable or processor-readable storage media may in this regard comprise any storage media that may be accessed by a computer or a processor. By way of example but not limitation, such non-transitory computer readable or processor-readable media may comprise RAM, ROM, EEPROM, FLASH memory, disk storage, magnetic storage devices, or the like. Disk storage, as used herein, comprises compact disc (CD), laser disc, optical disc, digital versatile disc (DVD), floppy disk, and Blu-ray Disc™, or other storage devices that store data magnetically or optically with lasers. Combinations of the above types of media are also included within the scope of the terms non-transitory computer-readable and processor-readable media. Additionally, any combination of instructions stored on the one or more non-transitory processor-readable or computer-readable media may be referred to herein as a computer program product.

Figure 5:
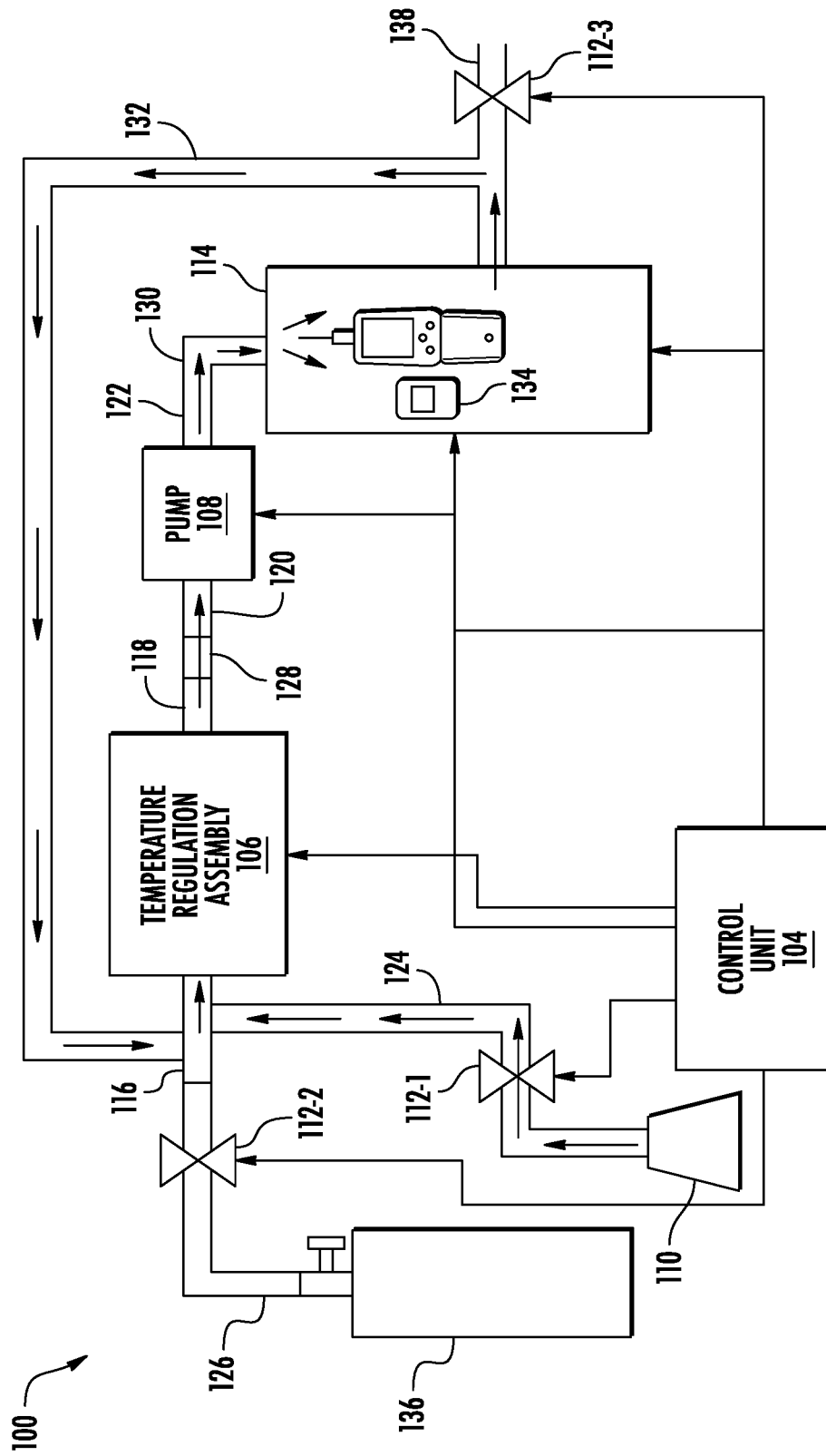
FIG. 5 illustrates flow of ambient air through a gas detector calibration system, according to one or more embodiments described herein.

FIG. 5 illustrates a flow of the ambient air in a gas detector calibration system, such as the gas detector calibration system 100, prior to calibration of the gas detector, in accordance with the example embodiments described herein. For flow of the ambient air, the valve and pump controller 210 closes the second valve 112-2 and the third valve 112-3 and opens the first valve 112-1 to allow flow of the ambient air from the atmospheric filter 110. The ambient air flows through the first conduit 124. The ambient air then enters the temperature regulation assembly 106 through the inlet 116. The ambient air is supplied to the pump 108 through the outlet 118, the third conduit 128 and the pump inlet 120. Through the pump outlet 122 and the fourth conduit 130, the ambient air flows into the chamber 114 for calibration of the gas detector 102. In an alternative embodiment, if there is no chamber 114, the ambient air is supplied to the gas detector 102, the gas detector being placed adjacent to an end of the fourth conduit 130 supplying the ambient air.

In an example, when the temperature of the gas detector 102 is not within the predefined temperature range, the ambient air may be supplied to the inlet 116 of the temperature regulation assembly 106 from the chamber 114 through the feedback conduit 132. The temperature of the ambient air is modified by the temperature regulation assembly 106 and is supplied to the pump 108. Thereafter, the ambient air is supplied to the chamber 114.

Figure 6:
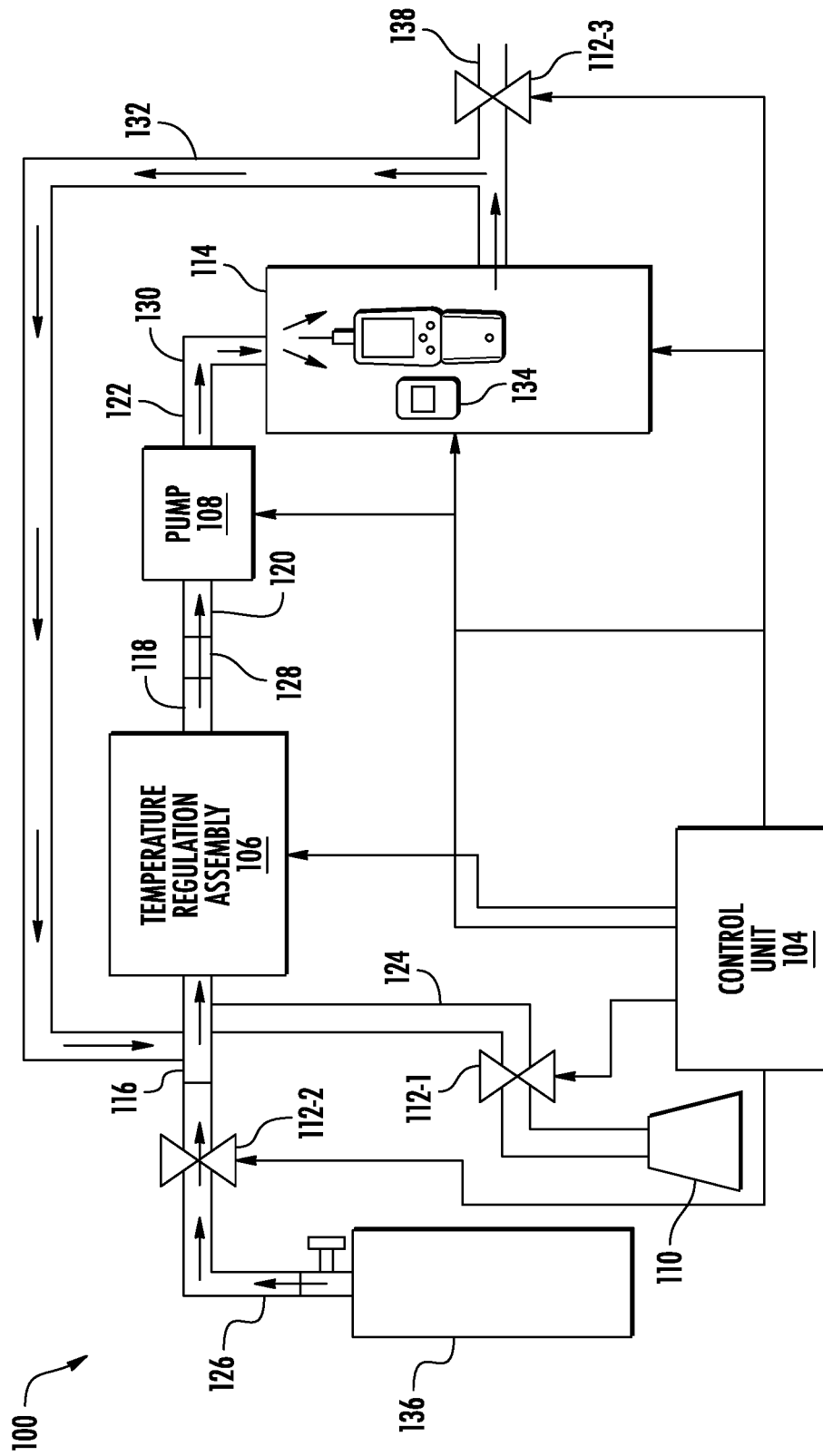
FIG. 6 illustrates flow of calibration gas through a gas detector calibration system, according to one or more embodiments described herein.

FIG. 6 illustrates a flow of the calibration gas in the gas detector calibration system 100 during calibration of the gas detector 102, in accordance with the example embodiments described herein. The valve and pump controller 210 may close the first valve 112-1 and the third valve 112-3 and open the second valve 112-2 to allow flow of the calibration gas from the gas container 136. The calibration gas flows through the second conduit 126. The calibration gas then passes through the temperature regulation assembly 106 through the inlet 116. The calibration gas is supplied to the pump 108 through the outlet 118, the third conduit 128 and the pump inlet 120. Through the pump outlet 122 and the fourth conduit 130, the calibration gas flows into the chamber 114. In an alternative embodiment, the ambient air is supplied to the gas detector 102 if there is no chamber. The gas detector is placed adjacent to the end of the fourth conduit 130 supplying the calibration gas.

In an example, when the calibration of the gas detector 102 is not at the desired level, the calibration gas may be supplied from the chamber 114 to the inlet 116 of the temperature regulation assembly 106 through the feedback conduit 132. The temperature of the calibration gas is modified by the temperature regulation assembly 106 and is supplied to the pump 108. Thereafter, the calibration gas is supplied to the chamber 114 for calibration of the gas detector 102.

Many modifications and other embodiments of the disclosure set forth herein will come to mind to one skilled in the art to which this disclosure pertains having the benefit of teachings presented in the foregoing descriptions and the associated drawings. Although the figures only show certain components of the apparatus and systems described herein, it is understood that various other components may be used in conjunction with the supply management system. Therefore, it is to be understood that the disclosure is not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

What is claimed is:

1. A calibration system for calibrating a gas detector, the calibration system comprising:
   a control unit;
   a temperature regulation assembly electrically connected with the control unit, wherein the temperature regulation assembly is configured to modify a temperature of ambient air, the ambient air being supplied to the gas detector;
   a temperature sensor electrically connected with the control unit;
   a set of valves comprising a first valve, a second valve, and a third valve; and
   a feedback conduit, wherein the control unit is configured to:
  determine whether a temperature of the gas detector is within a predefined temperature range;
  calibrate the gas detector in an instance in which the temperature is within the predefined temperature range;
  open the first valve to allow flow of the ambient air to the temperature regulation assembly for regulating the temperature of the ambient air; and
  close each of the second valve and the third valve, wherein the second valve is to control flow of a calibration gas to the temperature regulation assembly from a gas container and the third valve is to control flow of the ambient air and the calibration gas through the feedback conduit to the temperature regulation assembly.

2. The calibration system of claim 1, further comprising a pump electrically connected with the control unit, the pump having a pump inlet and a pump outlet.

3. The calibration system of claim 2, further comprising a chamber connected to the pump outlet of the pump, wherein the chamber encloses the temperature sensor and the gas detector.

4. The calibration system of claim 3, further comprising a first conduit, a second conduit, and a third conduit, wherein the first conduit is connected to an inlet of the temperature regulation assembly, the second conduit is connected to an outlet of the temperature regulation assembly, and the third conduit is connected with the inlet of the temperature regulation assembly to supply the calibration gas.

5. The calibration system of claim 4, wherein a first end of the feedback conduit is attached to the chamber and a second end is attached to the temperature regulation assembly.

6. The calibration system of claim 5, wherein the feedback conduit has an exhaust conduit to release the ambient air and the calibration gas.

7. The calibration system of claim 6, wherein the first valve is connected to the first conduit to control flow of the ambient air through the first conduit, the second valve is connected to the third conduit to control flow of the calibration gas, and the third valve is connected to the exhaust conduit of the feedback conduit to control flow of the ambient air and the calibration gas.

8. The calibration system of claim 4, further comprising an atmospheric filter coupled to the first conduit, wherein the atmospheric filter is configured to receive the ambient air and supply the ambient air to the temperature regulation assembly through the first conduit.

9. The calibration system of claim 1, wherein the control unit is configured to modify heating or cooling performed by the temperature regulation assembly to modify the temperature of the ambient air.

10. The calibration system of claim 1, wherein the temperature regulation assembly comprises a heating unit and a cooling unit, wherein the heating unit is configured to heat the ambient air and the cooling unit is configured to cool the ambient air.

11. A method of calibration of a gas detector, the method comprising:
  causing, by a control unit, a temperature regulation assembly to modify a temperature of ambient air, the ambient air being supplied to the gas detector;
  receiving, by the control unit, a signal indicative of a temperature of the gas detector from a temperature sensor;
  determining, by the control unit, whether the temperature of the gas detector is within a predefined temperature range;
  calibrating the gas detector when the temperature of the gas detector is within the predefined temperature range;
  causing, by the control unit, a first valve to open, wherein the first valve is to allow flow of the ambient air to the temperature regulation assembly for regulating the temperature of the ambient air; and
  causing, by the control unit, each of a second valve and a third valve to close, wherein the second valve is to control flow of a calibration gas to the temperature regulation assembly from a gas container and the third valve is to control flow of the ambient air and the calibration gas through a feedback conduit to the temperature regulation assembly.

12. The method of claim 11, wherein calibrating the gas detector comprises:
  causing, by the control unit, the temperature regulation assembly to modify a temperature of the calibration gas; and
  causing, by the control unit, a pump to supply the calibration gas to the gas detector for calibration.

13. The method of claim 11, comprising causing, by the control unit, a pump to supply the ambient air for regulating temperature of the gas detector, when the temperature of the gas detector is not within the predefined temperature range in response to determining the temperature of the gas detector.

14. The method of claim 11, wherein receiving the signal indicative of the temperature comprises causing, by the control unit, the temperature sensor to determine the temperature of the gas detector.

15. The method of claim 11, wherein the predefined temperature range is from about 30° C. to about 60° C.

16. The method of claim 11, comprising:
  causing, by the control unit, the second valve to open, wherein the second valve is to control flow of the calibration gas to the temperature regulation assembly from the gas container; and
  causing, by the control unit, each of the first valve and the third valve to close, wherein the first valve is to allow flow of the ambient air to the temperature regulation assembly and the third valve is to control flow of the ambient air and the calibration gas through the feedback conduit.

17. The method of claim 11, further comprising, causing, by the control unit, the temperature regulation assembly to modify heating or cooling of the ambient air.

18. The method of claim 11, wherein the control unit causes the temperature regulation assembly to modify the temperature of the ambient air by regulating heating or cooling performed by the temperature regulation assembly.

19. A calibration system for calibrating a gas detector, the calibration system comprising:
  a control unit;
  a temperature regulation assembly electrically connected with the control unit, the temperature regulation assembly having an inlet and an outlet;
  a pump electrically connected with the control unit, the pump having a pump inlet and a pump outlet, wherein the outlet of the temperature regulation assembly is fluidly coupled to the pump inlet;
  a temperature sensor electrically connected with the control unit; and
  a chamber fluidly coupled to the pump outlet of the pump, wherein the chamber encloses the temperature sensor and the gas detector, the temperature sensor being in proximity to the gas detector to measure a temperature of the gas detector, and wherein the chamber provides a closed environment to the gas detector for calibration and insulates the gas detector from outside temperature, wherein the control unit is configured to calibrate the gas detector in an instance in which the temperature of the gas detector is within a predefined temperature range.

20. The calibration system of claim 19, wherein the temperature regulation assembly is configured to:
receive ambient air through the inlet of the temperature regulation assembly;
modify a temperature of the ambient air; and
supply the ambient air, having the modified temperature, to the gas detector.

* * * * *